Sept. 28, 1965 E. S. BOERNER Plant Pat. 2,553
ROSE PLANT
Filed May 25, 1964
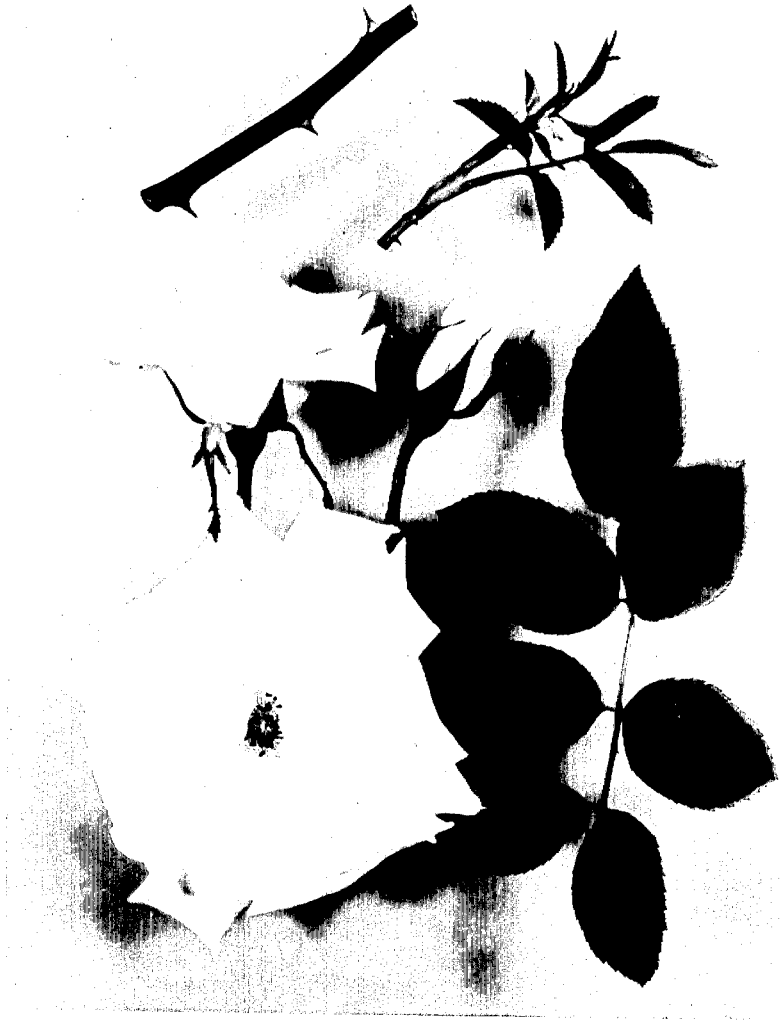
Inventor.
E. S. Boerner
By: Robb & Robb
Attorneys.

United States Patent Office

Plant Pat. 2,553
Patented Sept. 28, 1965

2,553
ROSE PLANT

Eugene S. Boerner, Newark, N.Y., assignor to Jackson & Perkins Company, Newark, N.Y., a corporation of New York Filed May 25, 1964, Ser. No. 370,140
1 Claim. (Cl. Plt.—14)

The present invention relates to a new and distinct variety of Rose plant of the hybrid tea class, which was originated by me by crossing the variety known as "Princess White" (Plant Patent No. 1,540) with the variety known as "White Queen" (Plant Patent No. 1,762).

The primary objective of this breeding was to produce a new rose variety which is suitable for both outdoor cultivation and for cut flower forcing, and which bears attractive White flowers of long-lasting qualities. This objective was fully achieved, along with other desirable improvements, as evidenced by the following unique combination of characteristics which are outstanding in the new variety and which distinguish it from its parents, as well as from all other varieties of which I am aware:

(1) Excellent suitability for cut flower forcing, with prolific production of attractive White flowers, especially when grown in the greenhouse for cut flower production;

(2) Good flower petalage, with the petals symmetrically arranged in a graceful manner, said petals being stiff and very resistant to rain and heat; and (3) Very long-lasting qualities of the flowers both on the plant and as cut flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetable growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Princess White."
*Pollen parent.*—"White Queen."

Classification:
*Botanic.*—Hybrid tea.
*Commercial.*—Hybrid tea.

*Flower*

(Observations made from specimens grown in a greenhouse at Newark, New York, in mid-morning during the early part of the month of April).

Blooming habit: Recurrent—continuous.

Bud:
*Size.*—Large.
*Form.*—Ovoid pointed.
*Color.*—When sepals first divide—Sea-Form Yellow, Plate 31. When petals begin to unfurl—Marguerite Yellow, Pate 30, lightly overcast at base with Sea-Foam Yellow, Plate 31. When half-blown: inside of petals—White, Plate 53, very lightly overcast with Marguerite-Yellow, Plate 30; reverse of petals—White, Plate 53, very lightly overcast with Sea-Foam Yellow, Plate 31 in the lower half of the petal.
*Sepals.*—Slightly branched; curl back when petals begin to unfurl. Color: inside—Light Turtle Green, Plate 32; outside—Biscay Green, Plate 17.

*Calyx.*—Color—Biscay Green, Plate 17. Shape—apple. Size—broad. Aspect—smooth. Odor when rubbed—none.
*Peduncle.* — Length — long. Aspect — rough. Strength—erect; heavy. Color—Rainette Green, Plate 31.
*Opening.*—Opens up well; is not affected by adverse weather conditions.

Bloom:
*Size.*—Large. Average size when fully expanded—5½ inches.
*Borne.*—Both singly and several together; many many blooms produced, especially when the plant is grown in the greenhouse as a cut flower variety.
*Stems.*—Long; strong.
*Form (when first open).*—High-centered. Permanence—retains its form to the end; outer petals curl back.
*Petalage.*—Very double (many petals and stamens hidden). Number of petals under normal conditions—from 55 to 60.
*Color.*—Center of flower—White, Plate 53. Outer petals—White, Plate 53. Base of petals (aiglet)—pale Chalcedony Yellow, Plate 17. Inside of petals — White, Plate 53. Reverse of petals — White, Plate 53.
*Discoloration.*—General tonality at end of first day—White, Plate 53. Second day—White, Plate 53. Third day—White, Plate 53.

Petals:
*Texture.*—Leathery and stiff; resistant to rain and heat; is not affected by wet or hot weather.
*Appearance.*—Inside—satiny. Outside—satiny.
*Form.*—Round; slightly notched.
*Arrangement.*—Imbricated and symmetrically arranged.
*Petaloids in center.*—Many; large.
*Persistence.*—Drop off cleanly.
*Fragrance.*—Moderate. Nature—tea (average hybrid tea scent).
*Lasting quality.*—On the plant—very long. As cut flower—very long.

*Genital organs*

Stamens, anthers: Medium size; many; regularly arranged around styles. Color—Mustard Yellow, Plate 16.

Stamens, filaments (threads): Medium length. Color—Primrose-Yellow, Plate 30.

Pollen: Color—cream color, Plate 16.

Styles: Bunched; uneven length; medium length; thin.

Stigmas: Color—Ochraceous Salmon, Plate 15.

Ovaries: All enclosed in calyx.

Hips: None.

Seeds: None.

*Plant*

Form: Bush.

Growth: Vigorous; upright.

Foliage: Compound of 3–5–7 leaflets.
*Size.*—Large.
*Quantity.*—Abundant.
*Color.*—New foliage: upper side—Chromium Green, Plate 32, very lightly overcast with Maroon, Plate 1; under side—Courge Green, Plate 17, overcast with Victoria Lake, Plate 1. Old foliage: upper side.—Dark Cress Green, Plate 31; under side—Light Bice Green, Plate 17.

*Shape.*—Oval pointed.
*Texture.*—Upper side — leathery. Under side — smooth.
*Ribs and veins.*—Ordinary.
*Edge.*—Serrated (saw toothed).
*Serration.*—Both double and single; small.
*Leaf stem.*—Color—Light Cress Green, Plate 31. under side—smooth.
*Stipules.*—Long; bearded.

Wood:

*New wood.*—Color—Absinthe Green, Plate 31. Bark—smooth.
*Old wood.*—Color—Bice Green, Plate 17. Bark—smooth.

Thorns:

*Thorns.*—Quantity: on main stalks from base — many; on laterals from stalk—many. Form—flat base; medium length; hooked downward. Color (when young)—Mignonette Green, Plate 31. Position—irregular.

*Prickles.*—Quantity: on main stalks—none. On laterals—none.
*Short needles.*—Quantity: on main stalks—none; on laterals—none.

I claim:

A new and distinct variety of rose plant of the hybrid tea class, substantially as herein shown and described, characterized particularly as to novelty by the unique combination of excellent suitability for cut flower forcing, with prolific production of attractive White flowers espeically when grown in the greenhouse for cut flower production, good flower petalage, with the petals symmetrically arranged in a graceful manner, said petals being stiff and very resistant to rain and heat, and very long-lasting qualities of the flowers both on the plant and as cut flowers.

No references cited.

ABRAHAM G. STONE, *Primary Examiner.*